United States Patent [19]

Braunweiler

[11] 4,356,733

[45] Nov. 2, 1982

[54] DOSING DEVICE FOR GAS CHROMATOGRAPHY

[75] Inventor: Max Braunweiler, Mannheim, Fed. Rep. of Germany

[73] Assignee: Siemens Aktiengesellschaft, Berlin and Munich, Fed. Rep. of Germany

[21] Appl. No.: 197,234

[22] Filed: Oct. 15, 1980

[30] Foreign Application Priority Data

Oct. 19, 1979 [DE] Fed. Rep. of Germany ....... 2942395

[51] Int. Cl.³ .............................................. G01N 1/14
[52] U.S. Cl. ............................. 73/863.11; 73/863.83
[58] Field of Search ........... 73/863.11, 863.73, 863.83, 73/864.83

[56] References Cited

U.S. PATENT DOCUMENTS

| 3,362,228 | 1/1968 | Stuben | 73/863.83 |
| 3,401,565 | 9/1968 | Stoll et al. | 73/863.11 |
| 3,715,058 | 2/1973 | Clymans | 73/863.83 |
| 4,128,008 | 12/1978 | Linenberg | 73/864.83 |

Primary Examiner—S. Clement Swisher
Attorney, Agent, or Firm—Kenyon & Kenyon

[57] ABSTRACT

In a dosing device for gas chromatography which includes a portion coupled to the sampling stream, a sample evaporation chamber, and a dosing plunger, the portion of the dosing plunger which carries the dosing volume is made of a highly heat conducting material and a high capacity current source is provided for heating the dosing plunger rapidly in the area of the dosing volume in order to quickly bring the dosing plunger to a high temperature such that heat will be transferred from the dosing plunger to the sample in the sample chamber and heat the sample.

14 Claims, 4 Drawing Figures

DOSING DEVICE FOR GAS CHROMATOGRAPHY

BACKGROUND OF THE INVENTION

1. Field of the Invention

The invention relates to a dosing device for gas chromatography with a dosing plunger which can be moved axially between a sampling position in the sample stream and a delivery position in a sample evaporation chamber connected to the separation column, and which is provided with a dosing volume measuring means in the form of a recess in the shank of the plunger.

2. The Prior Art

Devices are known for preparing liquid samples for gas chromatography analysis in which it is desired to evaporate the liquid sample in an electrically heated evaporation chamber as quickly and completely as possible so that the gas can be fed to the separation column without delay to obtain better separation results.

Difficulties arise, however, if sample liquids with a high boiling point are to be evaporated; the high temperatures required for this purpose can be obtained in the externally heated evaporation chamber only with difficulty at the rate of temperature rise necessary for the sudden evaporation. The maximum evaporation temperature is also limited by the critical heat-carrying capacity of the materials of the device, particularly of the seals in the plunger feedthroughs.

OBJECTS AND SUMMARY OF THE INVENTION

A principal object of this invention is to improve known dosing devices, which are usually provided with a program-controlled positioning drive for the movement of the plunger, in such a manner that fast evaporation of the sample can also be achieved for sample substances with a high boiling point.

Further objects will be apparent from the following written description together with the drawings.

According to this invention, the part of the plunger that carries the dosing recess is made of highly heat conducting material and is so constructed and arranged as to be directly heatable from a high-capacity current source. This can be accomplished, for instance, by electric resistance heating means, including an electric heater winding or an insulated heating element attached in the interior or in the wall of the plunger.

In a preferred embodiment, the part of the plunger in which the dosing recess is located comprises an electric heating resistance. Power from an electric power source capable of supplying on the order of several hundred watts is fed to the electric heating resistance in pulses with a pulse duration of up to 2 sec. As a result, a temperature of up to 500° C. is obtained during the heating pulse so that the sample is evaporated almost instantaneously and is flushed by means of carrier gas from the evaporation chamber into the separation column.

Since the plunger cools off relatively quickly, it can be brought into the sampling position again long before the end of the analysis time. It is, therefore, possible to carry out a large number of dosings automatically in rapid succession.

DETAILED DESCRIPTION OF THE INVENTION

Figure 1:
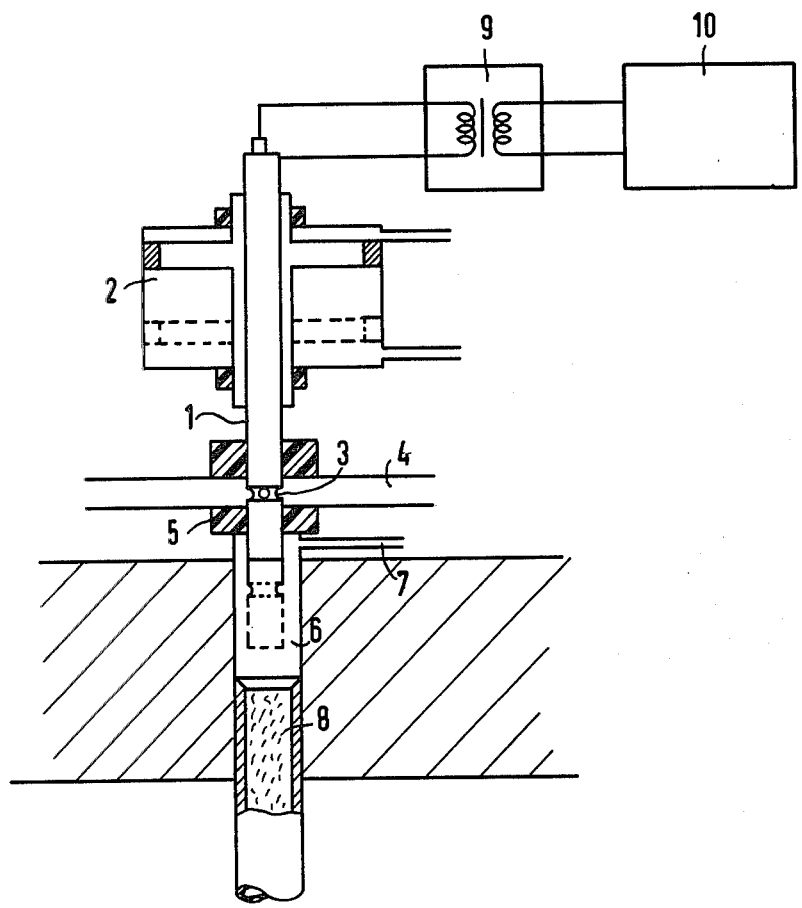
FIG. 1 shows a schematic view of apparatus that includes a dosing device according to the invention.

The dosing device shown in FIG. 1 consists essentially of a dosing plunger 1, which is movable by means of a positioning drive 2 between upper and lower end positions. A dosing recess 3 in the form of a circular slot, or annular groove, is arranged in the lower end section of the cylindrical shank of the dosing plunger 1.

The dosing plunger is shown in its upper end position in which the section of the plunger provided with the dosing recess 3 is positioned in a sampling space 4 containing the sample liquid. The dosing plunger can be moved into its lower end position, shown in dashed lines, by appropriate control of the positioning drive 2 to move the lower end section with the dosing recess 3 and the sample liquid contained therein through a teflon seal 5, into an evaporation chamber 6. This chamber receives carrier gas from a carrier gas source by way of a connection 7. A gas chromatography separating column 8 below the plunger receives the carrier gas and evaporated sample.

In order to evaporate the liquid sample in the dosing volume 3 rapidly, the section of the dosing plunger 1 carrying the dosing recess 3 is made as an electric heating resistance and is connected to a current source 9 capable of supplying power in the order of magnitude of several hundred watts. This makes it possible to attain a high heating rate of approximately 250°/sec for the sample contained in the dosing recess 3. This causes the sample to be evaporated almost instantly so that it can be flushed into the separation column 8 by the carrier gas.

With a heating pulse 2 sec. long, plunger wall temperatures of up to 500° can thus be obtained, so that it is possible to evaporate high boiling point substances rapidly. The duration of the heating pulse can be set by means of the control unit 10 as a function of the component of the liquid sample having the highest boiling point, and the dosing device shown can be operated fully automatically by simple means, so that a large number of dosings can be carried out automatically without further attention.

Figure 2:
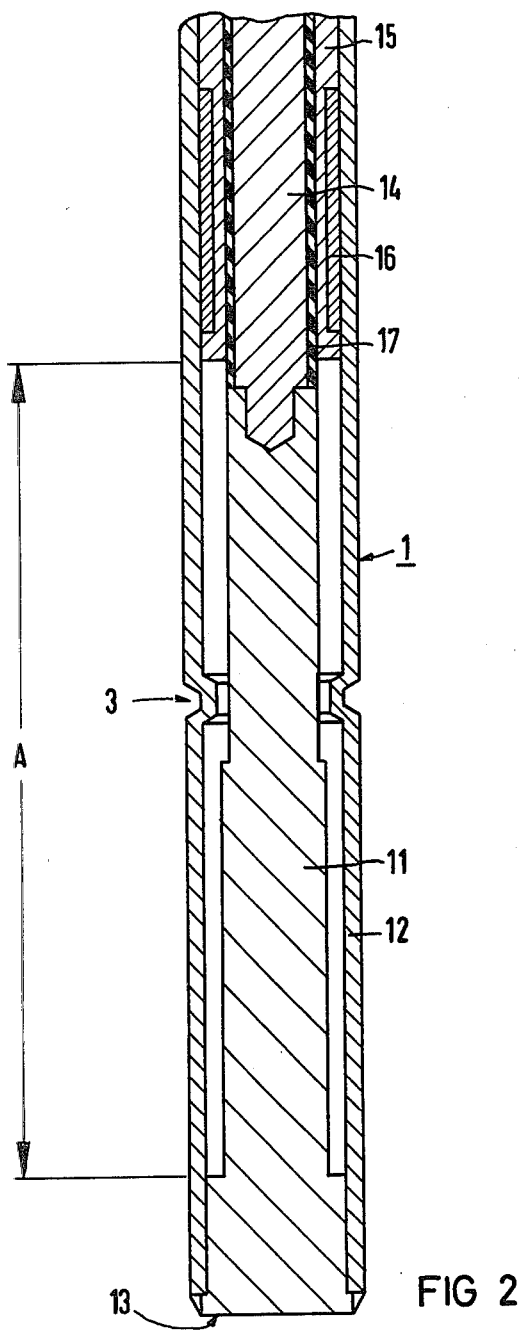
FIG. 2 illustrates an embodiment example of a heatable dosing plunger for use in the dosing device in FIG. 1.

FIG. 2 shows a longitudinal cross section of a preferred embodiment of the dosing plunger 1. At its lower end section, it consists of a core 11 and a relatively thin-walled sleeve 12 which extends over the core and is coaxially spaced therefrom. The dosing recess 3 is a circular slot formed as an indentation in the sleeve 12.

The core 11 and the sleeve 12 consist of the same corrosion-resistant material, preferably an alloy steel, and are electrically and mechanically connected to each other at the tip 13 of the dosing plunger 1. At its upper end, the core 11 is connected to a copper rod 14, which is coaxially arranged in the hollow dose plunger 1 and serves as means for connecting the core to a terminal of the current source 9 (FIG. 1). The other terminal of the current source is connected to a hollow cylinder 15 of copper or another highly conducting material inserted into the hollow dosing plunger 1. The hollow cylinder 15 is connected to the upper end of the hollow sleeve 12 by means of silver solder 16 to secure a low impedance connection for good current transfer and is electrically insulated from the copper rod 14 by an insulating layer 17.

The cross-sectional dimensions and the choice of materials in the dosing plunger 1 are selected so that the core 11 and the section of the sleeve 12 containing the dosing recess 3 have approximately the same electric resistance. By forming the dosing recess 3 as an indentation rather than by grinding away enough of the sleeve material to form a recess of the same volume, which would reduce the wall thickness of the sleeve at the recess, the region of the sleeve 12 at the dosing recess 3 will not be subjected to excessive heat.

When current is supplied via the copper rod 14 and the hollow cylinder 15, the core 11 and the sleeve 12 act as a series circuit of resistors, so that part A of the plunger 1 is heated very quickly and the liquid sample held in the dosing recess 3 evaporates. After the current is switched off, the heatable part A cools off quickly, so that the dosing plunger 1 can be run into its upper end position to receive another sample.

Figure 3:
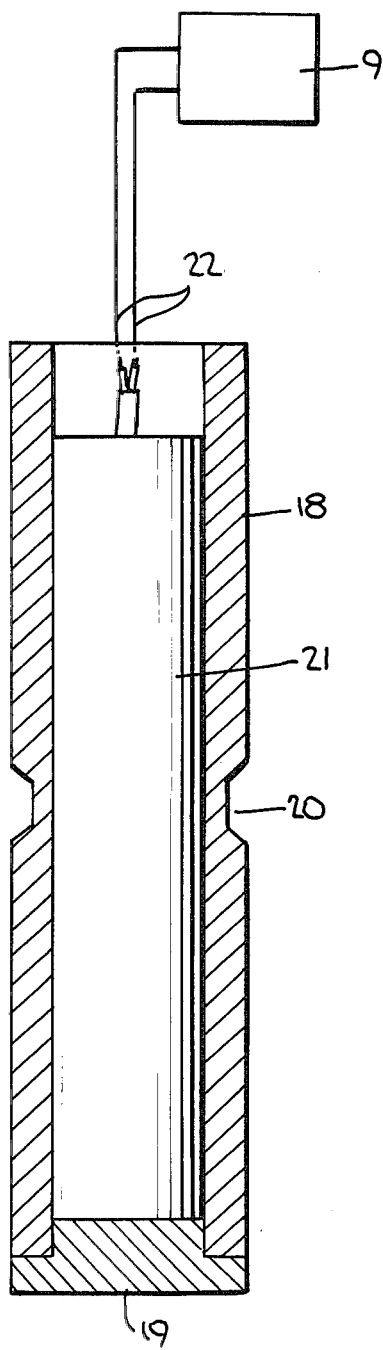
FIG. 3 is a cross sectional view of a modified embodiment of a dosing plunger for use in the dosing device in FIG. 1.

FIG. 3 shows the lower part of a modified dosing plunger 18 similar to the dosing plunger 1 in FIG. 1. The dosing plunger 18 is a hollow cylinder closed at its lower end by a cover 19 and having an annular groove 20 formed as a dosing recess approximately mid-way along the length of the cylinder. A cylindrical heating cartridge 21 of a commercially known type substantially fills the interior of the dosing plunger 18 and is provided with electrical lines 22 to be connected to the current source 9. Contrary to the dosing recess 3 in the embodiment in FIG. 2, the groove, or dosing recess 24 in FIG. 3 is formed by reducing the thickness of the wall of the plunger 18. However, this has the advantage of allowing the dosing recess to heat more quickly than it would if the wall of the plunger 18 were merely indented as in FIG. 2, because the heat in the plunger in FIG. 3 is provided by the cartridge 20 rather than by current flowing longitudinally along the outer wall of the plunger 18. The dosing plunger of the type shown in FIG. 3 is especially simple and inexpensive to manufacture.

Figure 4:
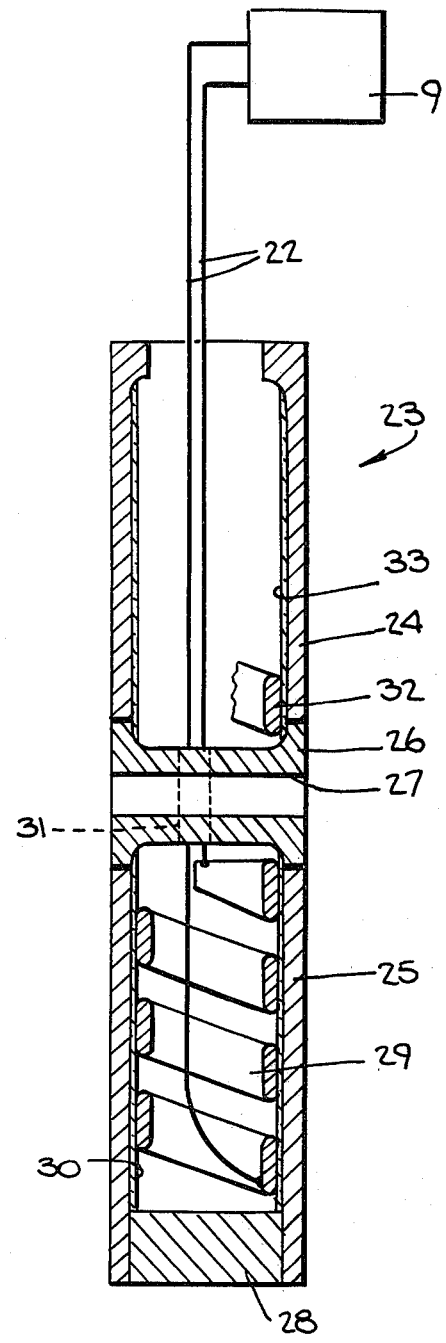
FIG. 4 shows a cross section of still another embodiment of a dosing plunger.

FIG. 4 shows an embodiment of a dosing plunger 23 that includes two thin walled hollow cylindrical parts 24 and 25 attached to opposite axial ends of a disc 26 of the same outer diameter as the cylinders 24 and 25. The cylinders 24 and 25 can be electrically welded to the disc 26 and all three of these parts are preferably made of material that is both very conductive to heat, and resistant to corrosion. The lower end of the cylinder 25 is closed by a plug 28 welded therein.

A dosing recess 27 is formed in the disc 26 as a transverse, cylindrical hole drilled therethrough with the axis of the transverse hole intersecting the axis of the disc 26. The cylindrical dosing recess 27 is oriented so that, when the plunger 23 is used in place of the plunger 1 in the apparatus in FIG. 1, the recess 24 will be free to receive the sampling liquid when the plunger 23 is raised to place the recess in line with the sampling space 4.

The disc 26 and its dosing recess 27 are heated by a heater element 29 in the form of helical, resistance heating element made of ribbon-shaped conductive material. In order to keep the heater element 29 from being short-circuited, the inner wall of the lower cylinder 25 is insulated by a material capable of withstanding the heat generated. For example, the inner wall of the cylinder 25 may be coated with a thin ceramic layer 30. This allows the disc 26 and the sample material contained in the dosing recess 27 to be heated quickly by current from the source 9, which is applied to the heater element 29 through openings 31 in the disc. These openings, of course, do not pass through the dosing recess 27.

A small part of another heater element 32 is shown in the upper cylinder 24. This heater element may be used in place of the winding 29 or in addition to it to heat the disc 26 and dosing sample material in the dosing recess 27. If the heater element 32 is used, a ceramic layer 33 may be applied to the inner wall of the cylinder 24 to insulate the cylinder from the heater element 32. The heater element 32 may be connected in series or in parallel with the element 29 to be supplied with current from the source 9 by means of the electric lines 22.

What is claimed is:

1. In a dosing device for gas chromatography which includes a portion coupled to the sampling stream, a sample evaporation chamber for coupling to the separation column of the gas chromatography device and a dosing plunger having a dosing volume, in the form of a recess formed therein, slidable between a sample-receiving position where it is in communication with the sample stream and a sample evaporating position where it is in communication with the sample evaporation chamber, the improvement comprising:
   (a) the portion of the dosing plunger carrying said dosing volume being made of a highly heat conducting material; and
   (b) means for heating said dosing plunger in the area of said dosing volume rapidly, said means including a high capacity current source, whereby, utilizing said high capacity current source, said dosing plunger can be quickly brought to a high temperature and heat transferred from said dosing plunger to the sample in the sample chamber for heating said sample.

2. The invention as defined in claim 1 in which the dosing plunger is substantially cylindrical and the dosing recess is intermediate the ends thereof and is open outwardly, the dosing device further including sealing means fitting around the plunger to separate the sample source from the evaporation chamber.

3. The invention as defined in claim 2 in which the dosing recess is an annular groove in the cylindrical surface of the plunger.

4. The invention as defined in claim 1 in which the plunger comprises:
   an electrically conductive cylindrical core;
   an electrically conductive tubular sleeve coaxial with the core and spaced outwardly therefrom over at least a part of the length of the plunger and connected electrically and mechanical to the core at one end to comprise, with the core, part of the electrical resistance heating means, the dosing recess comprising an annular recess in the sleeve intermediate the ends thereof.

5. The invention as defined in claim 4 in which the annular recess is defined by an indentation in the outer surface of the sleeve.

6. The invention as defined in claim 1 in which the core is made of corrosion-resistant material and the sleeve is made of the same corrosion-resistant material, and further including terminal means comprising:
(a) a first terminal comprising a copper rod mechanically connected to extend from the end of the core distal from the one end thereof and electrically connected to the core, the core and the copper rod comprising an extended inner portion of the plunger; and
(b) a second terminal comprising a hollow copper tube surrounding a part of the extended inner portion of the plunger and radially spaced therefrom, the hollow copper tube being mechanically and electrically connected to an end portion of the sleeve distal from the one end thereof said first and second terminals coupled to said current source.

7. The invention as defined in claim 1 wherein said high-capacity current source comprises a pulse source of electric current pulses to supply electric heating power on the order of magnitude of several hundred watts to the plunger in pulses, each of the pulses having a duration of less than aproximately two seconds.

8. The invention as defined in claim 1 in which:
the dosing plunger comprises first and second hollow cylindrical portions and an intermediate member therebetween; and
the heating means comprises an electrical resistance winding in at least one of the cylindrical portions and in heat-conductive contact with the inner wall thereof.

9. The invention as defined in claim 8 in which the heating means comprises:
a first electrical resistance winding in the first cylindrical portion; and
a second electrical resistance winding in the second cylindrical portion, the cylindrical portions being electrically conductive and comprising electrical insulating heat-conductive coatings on the respective inner walls thereof.

10. The invention as defined in claim 8 in which the intermediate member has substantially the same outer diameter as the first and second cylindrical portions and the dosing recess comprises a cylindrical hole extending therethrough transverse to the axis of the dosing plunger.

11. The invention according to claim 1, wherein at least the portion of said plunger carrying said dosing volume forms part of an electric heating resistance adapted to be coupled across said high-capacity current source.

12. The invention according to claim 1, wherein said plunger is hollow at least in an area adjacent said volume, said plunger thereby having an inner wall and an outer wall, said outer wall, in the area of said volume being in contact with the sample, and wherein said means for heating include a resistance heating element disposed inside said plunger.

13. The invention according to claim 12, wherein said winding is insulated, said insulated winding being in contact with said inner wall, whereby heat from said resistance heating element will be transferred from said inner wall through said plunger to said outer wall to evaporate the sample.

14. The invention as defined in claim 4, wherein said current source is coupled to the end of the core and the end of the sleeve, respectively, distal from the one end thereof, said core and sleeve thereby forming resistances in series with each other.

* * * * *